(12) United States Patent  
Korfhage

(10) Patent No.: US 9,133,508 B2  
(45) Date of Patent: Sep. 15, 2015

(54) METHOD FOR ISOTHERMAL AMPLIFICATION OF NUCLEIC ACIDS

(75) Inventor: Christian Korfhage, Langenfeld (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 13/816,081

(22) PCT Filed: Aug. 9, 2011

(86) PCT No.: PCT/EP2011/063686  
§ 371 (c)(1),  
(2), (4) Date: Feb. 8, 2013

(87) PCT Pub. No.: WO2012/020015  
PCT Pub. Date: Feb. 16, 2012

(65) Prior Publication Data  
US 2013/0224799 A1   Aug. 29, 2013

Related U.S. Application Data

(60) Provisional application No. 61/372,333, filed on Aug. 10, 2010.

(30) Foreign Application Priority Data

Aug. 10, 2010   (EP) .................... 10172400

(51) Int. Cl.  
*C12P 19/34* (2006.01)  
*C12Q 1/68* (2006.01)  
*C12N 11/04* (2006.01)

(52) U.S. Cl.  
CPC .............. *C12Q 1/6844* (2013.01); *C12N 11/04* (2013.01); *C12P 19/34* (2013.01); *C12Q 1/6848* (2013.01)

(58) Field of Classification Search  
CPC ....................................................... C12P 19/34  
USPC ....................................................... 435/91.2  
See application file for complete search history.

(56) References Cited

U.S. PATENT DOCUMENTS

| | | | | |
|---|---|---|---|---|
| 4,458,006 | A | | 7/1984 | Donges ............ 430/283 |
| 4,582,788 | A | | 4/1986 | Erlich ............... 435/6 |
| 4,582,789 | A | | 4/1986 | Sheldon, III ....... 435/6 |
| 5,413,924 | A | * | 5/1995 | Kosak et al. ........ 435/177 |
| 5,643,764 | A | | 7/1997 | Kosak ............... 435/91.1 |
| 6,903,195 | B1 | * | 6/2005 | Kiefer et al. ....... 530/387.1 |
| 2003/0228616 | A1 | * | 12/2003 | Arezi et al. ........ 435/6 |
| 2006/0068398 | A1 | | 3/2006 | McMillan .......... 435/6 |
| 2007/0117114 | A1 | * | 5/2007 | Rashtchian et al. ... 435/6 |
| 2009/0017453 | A1 | | 1/2009 | Maples ............. 435/6 |
| 2009/0081670 | A1 | | 3/2009 | Maples ............. 435/6 |

FOREIGN PATENT DOCUMENTS

| | | |
|---|---|---|
| EP | 0 201 184 | 12/1986 |
| EP | 0 320 308 | 6/1989 |
| EP | 0 877 094 | 11/1998 |
| WO | WO 98/00530 | 1/1998 |
| WO | WO 2007/120808 | 10/2007 |
| WO | WO 2008/036544 | 3/2008 |
| WO | WO 2008/090340 | 7/2008 |

OTHER PUBLICATIONS

An L, et al. (2005) Characterization of a thermostable UvrD helicase and its participation in helicase-dependent amplification. J Biol Chem. 280(32):28952-28958.  
Beaucage SL, et al. (1981) Deoxynucleoside Phosphoramidites—A New Class of Key Intermediates for Deoxypolynucleotide Synthesis. Tetrahedron Letters. 22(2):1859-1862.  
Chetverina HV, et al. (1993) Cloning of RNA molecules in vitro. Nucleic Acids Res. 21(10):2349-2353.  
Dafforn A, et al. (2004) Linear mRNA amplification from as little as 5 ng total RNA for global gene expression analysis. Biotechniques. 37(5):854-857.  
Dean FB, et al. (2002) Comprehensive human genome amplification using multiple displacement amplification. Proc Natl Acad Sci USA. 99(8):5261-5266.  
Kievits T, et al. (1991) NASBA isothermal enzymatic in vitro nucleic acid amplification optimized for the diagnosis of HIV-1 infection. J Virol Methods. 35(3):273-286.  
Liu D, et al. (1996) Rolling Circle DNA Synthesis: Small Circular Oligonucleotides as Efficient Templates for DNA Polymerases. J Am Chem Soc. 118(7):1587-1594.  
Mullis K, et al. (1986) Specific enzymatic amplification of DNA in vitro: the polymerase chain reaction. Cold Spring Harb Symp Quant Biol. 51(Pt 1):263-273.  
Notomi T, et al. (2000) Loop-mediated isothermal amplification of DNA. Nucleic Acids Res. 28(12):E63.  
Piepenburg O, et al. (2006) DNA detection using recombination proteins. PLoS Biol. 4(7):e204.  
Rychlik W, et al. (1990) Optimization of the annealing temperature for DNA amplification in vitro. Nucleic Acids Res. 18(21):6409-6412. Erratum in: Nucleic Acids Res. 19(3):698 (1991).  
Vincent M, et al. (2004) Helicase-dependent isothermal DNA amplification. EMBO. 5(8):795-800.  
Vuorinen P, et al. Direct detection of Mycobacterium tuberculosis complex in respiratory specimens by Gen-Probe Amplified Mycobacterium Tuberculosis Direct Test and Roche Amplicor Mycobacterium Tuberculosis Test. J Clin Microbiol. 33(7):1856-1859, (1995).  
Walker GT, et al. (1992) Strand displacement amplification—an isothermal, in vitro DNA amplification technique. Nucleic Acids Res. 20(7):1691-1696.  
Wang G, et al. (2004) DNA amplification method tolerant to sample degradation. Genome Res. 14(11):2357-2366.  
Wu DY, et al. (1989) The ligation amplification reaction (LAR)—amplification of specific DNA sequences using sequential rounds of template-dependent ligation. Genomics. 4(4):560-569.

(Continued)

*Primary Examiner* — Ardin Marschel  
(74) *Attorney, Agent, or Firm* — Ballard Spahr LLP

(57) ABSTRACT

A method is disclosed for improved isothermal amplification of nucleic acids comprising the step of release of an essential component from a matrix under predetermined conditions. Furthermore, the invention relates to a kit comprising mesophilic enzyme and a matrix with embedded essential components for isothermal amplification. A composition comprising a matrix and a mesophilic enzyme and a method for embedding a mesophilic enzyme are disclosed as well.

11 Claims, 2 Drawing Sheets

(56) References Cited

OTHER PUBLICATIONS

Figure 1:
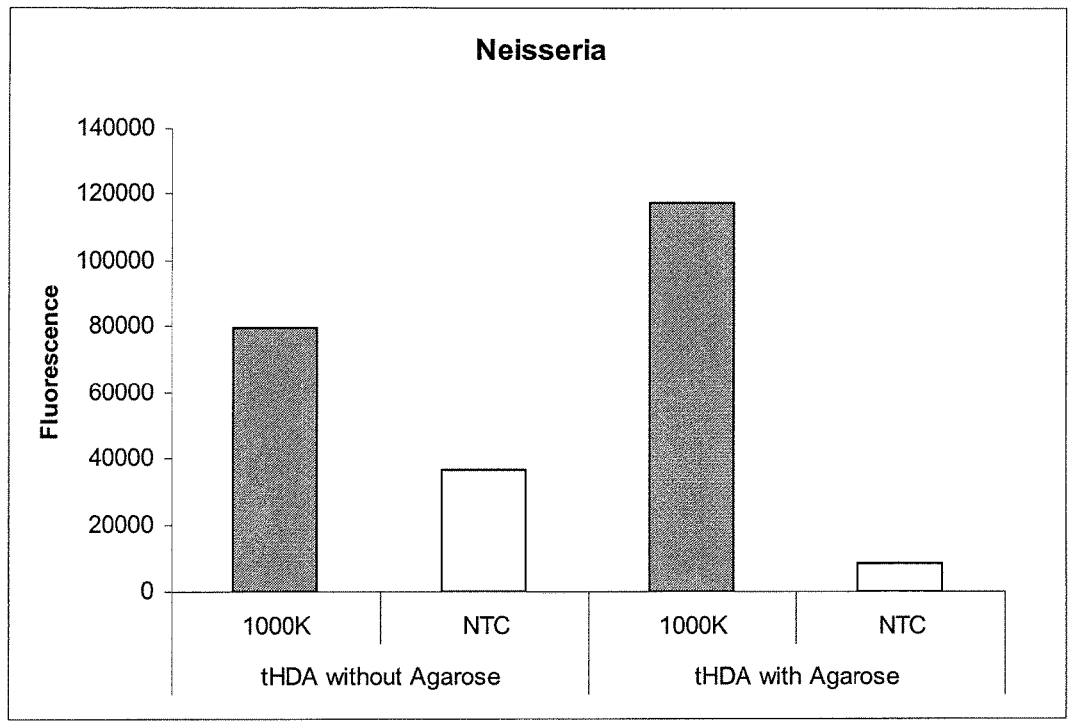
Figure 1:
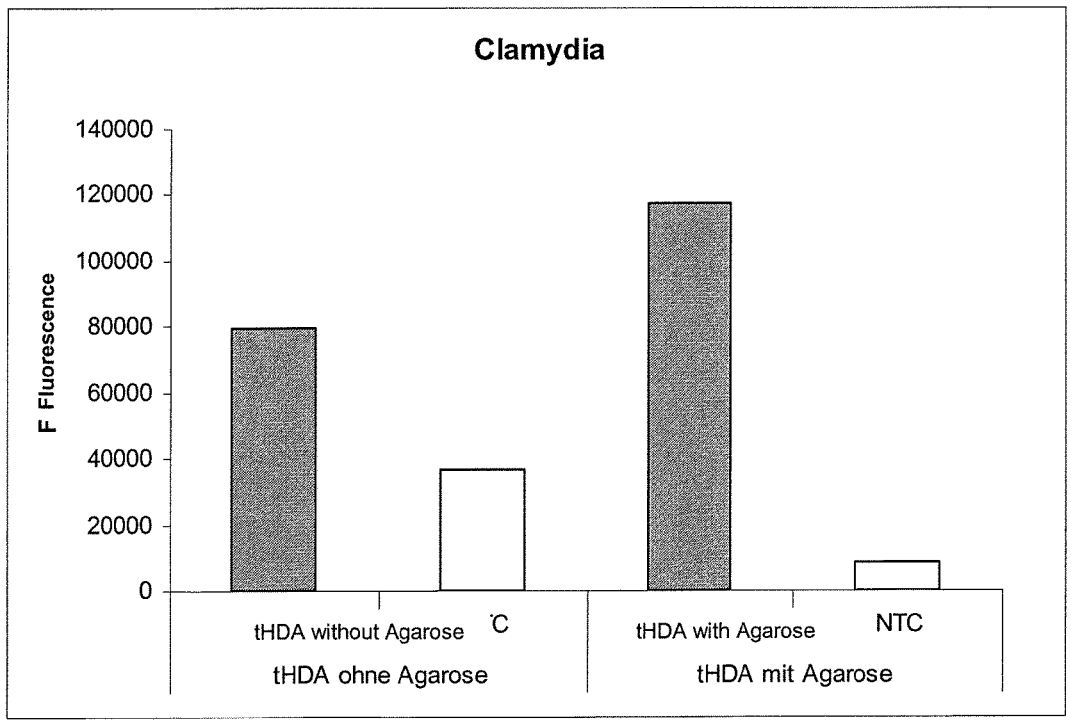

Zintz CB, et al. (1991) Rapid re-amplification of PCR products purified in low melting point agarose gels. Biotechniques. 11(2):158-162.

Rules 161(1) and 162 EPC Communication issued on Mar. 19, 2013 for EP Patent Application No. 11751567.6, which claims priority PCT/EP2011/063686 filed on Aug. 9, 2011 and published as WO 2012/020015 on Feb. 16, 2012 (Applicant Qiagen GmbH // Inventor—C. Korfhage) (2 pages).

International Preliminary Report on Patentability issued Feb. 12, 2013 for International Application No. PCT/EP2011/063686 filed on Aug. 9, 2011 and published as WO 2012/020015 on Feb. 16, 2012 (Applicant Qiagen GmbH // Inventor—C. Korfhage) (7 pages).

Written Opinion issued Feb. 10, 2013 for International Application No. PCT/EP2011/063686 filed on Aug. 9, 2011 and published as WO 2012/020015 on Feb. 16, 2012 (Applicant Qiagen GmbH // Inventor—C. Korfhage) (6 pages).

International Search Report issued Nov. 4, 2011 for International Application No. PCT/EP2011/063686 filed on Aug. 9, 2011 and published as WO 2012/020015 on Feb. 16, 2012 (Applicant Qiagen GmbH // Inventor—C. Korfhage) (5 pages).

* cited by examiner a)

b)

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:

-continued

<223> OTHER INFORMATION: synthetic construct

<400> SEQUENCE: 1
acccgatata atccgtcctt ca                                          22

<210> SEQ ID NO 2
<211> LENGTH: 22
<212> TYPE: DNA
<213> ORGANISM: Artificial Sequence
<220> FEATURE:
<223> OTHER INFORMATION: synthetic construct

<400> SEQUENCE: 2
cggctcctta ttcggtttaa cc                                          22

<210> SEQ ID NO 3
<211> LENGTH: 25
<212> TYPE: DNA
<213> ORGANISM: Artificial Sequence
<220> FEATURE:
<223> OTHER INFORMATION: synthetic construct

<400> SEQUENCE: 3
cgtccttcaa catcagtgaa aatcg                                       25

<210> SEQ ID NO 4
<211> LENGTH: 27
<212> TYPE: DNA
<213> ORGANISM: Artificial Sequence
<220> FEATURE:
<223> OTHER INFORMATION: synthetic construct

<400> SEQUENCE: 4
aggcgattta aaaccaagg tcgatgt                                      27

<210> SEQ ID NO 5
<211> LENGTH: 27
<212> TYPE: DNA
<213> ORGANISM: Artificial Sequence
<220> FEATURE:
<223> OTHER INFORMATION: synthetic construct

<400> SEQUENCE: 5
gaagaaattg atccaacacc cttatcg                                     27

<210> SEQ ID NO 6
<211> LENGTH: 27
<212> TYPE: DNA
<213> ORGANISM: Artificial Sequence
<220> FEATURE:
<223> OTHER INFORMATION: synthetic construct

<400> SEQUENCE: 6
ccgtatgtgg aatgtcgaac tcatcgg                                     27

<210> SEQ ID NO 7
<211> LENGTH: 26
<212> TYPE: DNA
<213> ORGANISM: Artificial Sequence
<220> FEATURE:
<223> OTHER INFORMATION: synthetic construct

<400> SEQUENCE: 7
atttgatgct gtccccggac gatatt                                      26

```
<210> SEQ ID NO 8
<211> LENGTH: 26
<212> TYPE: DNA
<213> ORGANISM: Artificial Sequence
<220> FEATURE:
<223> OTHER INFORMATION: synthetic construct

<400> SEQUENCE: 8
cattctggga gcttcatctg gacctg                                          26
```

METHOD FOR ISOTHERMAL AMPLIFICATION OF NUCLEIC ACIDS

CROSS REFERENCE TO RELATED APPLICATIONS

The present application is a National Phase Application of International Application No. PCT/EP2011/063686, filed Aug. 9, 2011, which claims priority to European Patent Application No. 10172400.3, filed Aug. 10, 2010 and U.S. Provisional Patent Application No. 61/371,333, filed Aug. 10, 2010, which applications are incorporated herein fully by this reference.

REFERENCE TO SEQUENCE LISTING

The Sequence Listing submitted Apr. 25, 2013 as a text file named "Substitute_Sequence_Listing" having a size of 2.0 kilobytes is hereby incorporated by reference pursuant to 37 C.F.R. §1.52(e)(5).

TECHNICAL FIELD

The present invention relates to the field of molecular biology, particularly to the field of isothermal nucleic acid amplification.

BACKGROUND OF THE INVENTION

The developments of methods for nucleic acid amplification and detection of amplification products have advanced the detection, identification, quantification and sequence analyses of nucleic acid sequences in recent years.

Nucleic acid analysis is useful for detection and identification of pathogens, detection of gene alteration leading to defined phenotypes, diagnosis of genetic diseases or the susceptibility to a disease, assessment of gene expression in development, diseases and in response to defined stimuli, as well as the various genome projects. Other applications of nucleic acid amplification methods are the detection of rare cells, detection of pathogens, and the detection of altered gene expression in malignancy, and the like. Nucleic acid amplification is potentially useful for both qualitative analysis, such as the detection of the presence of defined nucleic acid sequences, and quantification of defined gene sequences. The latter is useful for assessment of and amount of pathogenic sequences as well as the determination of gene multiplication or deletion, as often found in cell transformation from normal to malignant cell type. The detection of sequence alterations in a nucleic acid sequence is important for the detection of mutant genotypes, as relevant for genetic analysis, the detection of mutations leading to drug resistance, pharmacogenomics, etc. Various methods for the detection of specific mutations include allele specific primer extension, allele specific probe ligation, and differential probe hybridization.

Although, detection of the presence of a defined nucleic acid sequence, and its sequence analysis, can be carried out by probe hybridization, the method generally lacks sensitivity when low amounts of the nucleic acid sequence is present in the test sample, such as a few molecules. One solution to this obstacle was the development of methods for generation of multiple copies of the defined nucleic acid sequence, which are suitable for further analysis. The methods for generation of multiple copies of a specific nucleic acid sequence are generally defined as target amplification methods.

There are many variations of nucleic acid amplification, for example, exponential amplification, linked linear amplification, ligation-based amplification, and transcription-based amplification. An example of exponential nucleic acid amplification method is polymerase chain reaction (PCR) which has been disclosed in numerous publications (see, for example, Mullis et al. Cold Spring Harbor Symp. Quant. Biol. 51:263-273 (1986); Mullis K. EP-B2 201 184; Mullis et al. U.S. Pat. No. 4,582,788). Examples of ligation-based amplification are the ligation amplification reaction (LAR), disclosed by Wu et al. in Genomics 4:560 (1989) and the ligase chain reaction, disclosed in EP-B1 0 320 308. Various methods of transcription-based amplification are disclosed.

The most commonly used target amplification method is the polymerase chain reaction (PCR), which is based on multiple cycles of denaturation, hybridization of two oligonucleotide primers, each to opposite strand of the target strands, and primer extension by a nucleotide polymerase to produce multiple double stranded copies of the target sequence. Many variations of PCR have been described, and the method is being used for amplification of DNA or RNA nucleic acid sequences, sequencing, mutation analysis and others. Thermocycling-based methods that employ a single primer have also been described. Other methods that are dependent on thermal cycling are the ligase chain reaction (LCR) and the related repair chain reaction (RCR). Target nucleic acid amplification in the thermal cycling based methods is carried out through multiple cycles of incubations at various temperatures. Although these methods are widely used, amplification methods that use a thermocycling process have the disadvantage of long lag times which are required for the thermocycling block to reach the "target" temperature for each cycle. Consequently, amplification reactions performed using thermocycling processes require a significant amount of time to reach completion.

The isothermal target amplification methods do not require a thermocycler, and are thus easier to adapt to common instrumentation platforms. However, the isothermal target amplification methods have several drawbacks. Isothermal amplification methods are error-prone. Besides the amplification of the target region unspecific amplification products appear due to mispairing of primers. To avoid the generation of these side products the reaction components are heated separately and mixed at higher temperatures, e.g. a mixture comprising primer, probe and target DNA is heated to the reaction temperature separately from a further mixture comprising buffer, polymerase, dNTPs and helicase. Such a method is laborious and complicated.

Therefore, there is a need for improved nucleic acid amplification methods that overcome these drawbacks. The invention provided herein fulfils this need and provides additional benefits.

DESCRIPTION OF THE INVENTION

The present invention provides a method for amplification of nucleic acids comprising the steps of:
i) providing at least the following reaction components:
   a) a mesophilic enzyme for amplifying nucleic acids under isothermal conditions;
   b) one or more primer for amplifying a target nucleic acid;
   c) dNTPs and/or NTPs;
   d) essential co-factors and/or reagents of the at least one enzyme for amplifying nucleic acids under isothermal conditions;
   e) a target nucleic acid;

wherein at least one of the reaction components a) to e) is embedded in a matrix, wherein said matrix disintegrates under predetermined conditions;

ii) incubating the reaction components under conditions which result in the disintegration of said matrix in order to obtain the reaction mixture;

iii) incubating the reaction mixture under conditions suited for the isothermal amplification reaction.

The present invention additionally relates to a kit for isothermal amplification of nucleic acids comprising:

a mesophilic enzyme for amplifying nucleic acids under isothermal conditions, a matrix which disintegrates at predetermined conditions;

wherein at least one component which is essential for an isothermal amplification of nucleic acids is embedded in said matrix.

The present invention further relates to a composition comprising:

a matrix which disintegrates at predetermined conditions; and a mesophilic enzyme for amplifying nucleic acids under isothermal conditions.

Also encompassed by the present invention is a method for embedding mesophilic enzymes for amplifying nucleic acids under isothermal conditions comprising the steps of:

i) providing a solubilised matrix;

ii) mixing said matrix with a solution comprising at least one mesophilic enzyme for amplifying nucleic acids under isothermal conditions to obtain a matrix-enzyme mixture;

iii) incubating the matrix-enzyme mixture under conditions allowing the solidification of the matrix to obtain the embedded mesophilic enzyme.

DETAILED DESCRIPTION OF THE INVENTION

Herein "mesophilic" means that an enzyme has an optimum temperature of 70° C. or less. In a preferred embodiment the at least one mesophilic enzyme for amplifying nucleic acids has an optimum temperature of 20° C. to 70° C., preferably 30° C. to 65° C., more preferably 37° C. to 60° C. Mesophilic enzymes are in most cases not thermostable, i.e. they are irreversibly inactivated after incubation at high temperatures. In an embodiment the mesophilic enzyme of the present invention is not thermostable. In context with the present invention irreversible inactivation of mesophilic enzyme at a high temperature means that the enzyme is incubated at temperatures above its optimum temperature. In one embodiment incubation at high temperature means incubation at a temperature of at least 50° C., preferably at a temperature of at least 60° C., more preferably at a temperature of at least 70° C. By "irreversible inactivation" it is meant that a certain degree of enzyme activity is lost. Furthermore, the inactivation is not necessarily a complete inactivation, i.e. a residual enzyme activity of 70% or less, preferably 40% or less, more preferably 10% or less can be observed after incubation of the mesophilic enzyme at high temperatures. The skilled artisan will recognize that the inactivation of the mesophilic enzyme at high temperatures may be dependent on the time for which the incubation takes place. Thus, in a preferred embodiment the mesophilic enzyme is irreversibly inactivated after incubation at high temperatures for at least 30 s, preferably at least 1 min, more preferably at least 5 min, even more preferably at least 15 min.

It will be understood by those skilled in the art that the method according to the present invention allows determining the starting point of an isothermal amplification reaction.

As an essential component of the reaction, e.g. an enzyme, is embedded into the matrix, it is separated from the other reaction compounds in the reaction buffer, e.g. the template nucleic acid. This allows defining the time point and/or condition under which the reaction shall start by disintegration of the matrix. The matrix according the present invention disintegrates at predetermined conditions, i.e. it releases embedded compounds when shifted to said conditions. The matrix may be for example disintegrated enzymatically, chemically or physically.

In one embodiment of the present invention the matrix disintegrates through a shift of the pH. In a preferred embodiment of the present invention the net charge of the matrix is changed by a change of the pH resulting in a release of the embedded essential component of the isothermal amplification reaction.

In a preferred embodiment the at least one reaction component embedded in the matrix is released by diffusion. This allows a constant release of the at least one embedded reaction component.

Furthermore, a constant release of the at least one embedded reaction component can be reached by enzymatic disintegration of the matrix. Thus, in a preferred embodiment of the present invention the matrix is disintegrated by the addition of an enzyme selected from the group comprising collagenase, hyaluronidase, agarase, alginase and amylase.

In one embodiment of the invention the matrix disintegrates at predetermined temperatures. In a preferred embodiment the matrix disintegrates at temperatures of 50° C. or more, preferably 60° C. or more, more preferably 65° C. or more. It is especially preferred that the predetermined temperature at which the matrix disintegrates is higher than the annealing temperature, i.e. approximately $T_m$, of the at least one primer, preferably of all primer. This allows a hot start isothermal amplification reaction, as the reaction does not start at temperatures at which the primers unspecifically bind to non target sequences. Thereby unspecific amplification products are diminished. Annealing temperature is the temperature above which the oligonucleotide primer and the DNA template melt or dissociate. The annealing temperature may vary with the sequence homology between the template and the primers and the length and the GC content of the primer and template. The annealing temperature at which 50% of a primer is annealed to its template as well as an optimal annealing temperature for a specific reaction can be calculated, for example as described in Rychlik et al., Nucleic Acids Research, 18:6401-6412, 1990. The annealing temperature of preferred primer is in the range from about 50° C. to 75° C., preferably between 55° C. and 65° C., more preferably between 55° C. and 60° C.

The skilled artisan knows matrixes suited for the present invention. In a preferred embodiment the matrix is selected from the group comprising polysaccharides, proteins, waxes and synthetic polymers. In a yet further preferred embodiment the matrix is selected from the group comprising agarose, low-melting agarose, pectin, amylose, agar-agar, xanthan, carrageen, guar, carubin, inulin, dextran, gelatine, fibrillar proteins (e.g. collagen), polyvinylalcohol, derivates of cellulose (e.g. carboxymethylcellulose).

In a preferred embodiment the matrix is agarose (including low melting agarose). Different agarose with different melting points are commercially available. Low melting point agarose melts or disintegrates at temperatures approximately greater than 60° C. High melting point agarose disintegrates at temperatures approximately greater than 90° C. Other forms of agarose are commercially available which exhibit melting points between 50° C. and 95° C. (e.g. Sigma Aldrich GmbH, Germany). By varying the type and/or concentration of a particular type of agarose, a variety of specific disintegration temperatures can be achieved, e.g. compositions having a disintegration temperature of 50° C. or more, preferably 60° C. or more, more preferably 65° C. or more. To achieve a desired disintegration temperature of an agarose composition, a type of agarose having a melting point in the desired disintegration temperature range. For example, if the desired disintegration temperature is approximately 63° C., low melting point agarose with a melting point of 65° C. is selected. Agarose solutions of various concentrations (e.g. 0.1% to 2.5%) are prepared in aqueous solution, e.g., water or buffer, heated to melting and cooled to gelling point in a reaction tube. The agarose reaction tubes are then reheated and the disintegration temperature can be determined. In this way, an appropriate agarose and its concentration can be selected. This selection process may be utilized to select a specific matrix type and concentration to achieve a desired composition according to the present invention. In a preferred embodiment of the present invention the matrix is a hydrogel comprising 0.1% to 4% (w/v) agarose, preferably 0.5% to 3% (w/v), more preferably 1.0% to 2% (w/v).

After disintegration of the matrix it preferably dissolves within the medium of the reaction, i.e. in the reaction buffer. In a preferred embodiment the matrix forms a hydrogel. Hydrogel (also called aquagel) is a network of water insoluble polymer chains interlinked by covalent bonds and/or ionic interactions. The polymers comprise hydrophilic compounds. Thus, in the presence of water the polymers soak water resulting in a volumetric expansion without loss of the integrity of the polymer network. Hydrogels are highly absorbent natural or synthetic polymers with a water content of 50% or more, preferably 70% or more, more preferably 80% or more, even more preferably 90% or more. In one embodiment the matrix disintegrates under predetermined conditions and forms a colloidal gel with water or buffer as the dispersion medium. In a further embodiment the matrix disintegrates by melting.

Variations of the above-described may be performed by those skilled in the art. The matrix, e.g., may be formed of a variety of materials, polymers, and the like, provided the matrix disintegrates at predetermined conditions and the matrix does not interfere with the isothermal amplification reaction. To test the compatibility of a matrix, the method according to the present invention is carried out with a potential matrix material and/or over a range of different matrix concentrations. The method is monitored for interference as compared with a matrix-free control.

At least one enzyme used in the methods, the kit or composition according to the present invention is a mesophilic enzyme. However, the matrix in which at least one essential compound is embedded, disintegrates at relative high temperatures. Mesophilic enzymes often are irreversibly inactivated at temperatures which are above their optimum temperature. The inventors unexpectedly found that a hot start procedure is possible with the method according to the present invention. Thus, in a preferred embodiment of the present invention the incubation temperature under step ii) is 1° C. to 50° C. higher than the incubation temperature of step iii), preferably 5° C. to 25° C. higher, more preferably 10° C. to 20° C. higher. However, in a further embodiment of the present invention the temperatures of step ii) and step iii) of the method of amplification according to the present invention are identical.

By "isothermal amplification reaction" in context of the present invention it is meant that the temperature does not significantly change during the reaction. In a preferred embodiment the temperature of the isothermal amplification reaction does not deviate by more than 10° C., preferably by not more than 5° C., even more preferably not more than 2° C.

Depending on the method of isothermal amplification of nucleic acids, different enzymes are required for the amplification reaction. Known isothermal methods for amplification of nucleic acids are e.g. helicase-dependent amplification (HDA) (Vincent et al.; "Helicase-dependent isothermal DNA amplification", EMBO reports 5(8): 795-800 (2004)), thermostable HDA (tHDA) (An, et al., "Characterization of a Thermostable UvrD Helicase and Its Participation in Helicase-dependent Amplification", Jour. Biol. Chem. 280(32): 28952-28958(2005)), strand displacement amplification (SDA) (Walker, et al., "Strand displacement amplification—an isothermal, in vitro DNA amplification technique," Nucleic Acids Res. 20(7):1691-6 (1992)), multiple displacement amplification (MDA) [Dean, et al., "Comprehensive human genome amplification using multiple displacement amplification", PNAS 99(8): 5261-5266 (2002)), rolling circle amplification (Liu, et al., "Rolling circle DNA synthesis: Small circular oligonucleotides as efficient templates for DNA polymerases," J. Am. Chem. Soc. 118:1587-1594 (1996)), single primer isothermal amplification (SPIA) [Dafforn, et al., "Linear mRNA amplification from as little as 5 ng total RNA for global gene expression analysis", Biotechniques 37(5):854-7 (2004)) restriction aided RCA [Wang, et al., "DNA amplification method tolerant to sample degradation", Genome Res. 14:2357-2366 (2004)], transcription mediated amplification (TMA) [Vuorinen, et al., "Direct detection of *Mycobacterium tuberculosis* complex in respiratory specimens by Gen-Probe Amplified *Mycobacterium Tuberculosis* Direct Test and Roche Amplicor PCR *Mycobacterium Tuberculosis* Test. J. Clin. Microbiol. 33: 1856-1859 (1995)], Nucleic Acid Sequence Based Ampification (NASBA) [Kievits, et al., "NASBA, isothermal enzymatic in vitro nucleic acid amplification optimized for the diagnosis of HIV-1 infection. J. Virol. Methods 35:273-286 (1991)] and amplification reactions using nicking enzymes, nicking enzyme amplification reaction (NEAR) [Maples, et al., "Nicking and extension amplification reaction for the exponential amplification of nucleic acids", US2009017453], amplification reactions using recombination proteins, recombinase polymerase amplification (RPA) [Piepenburg, et al., "DNA Detection Using Recombination Proteins", PLoS Biol. 4(7): e204 (2004)], and Loop-mediated isothefinal amplification (LAMP) [Notomi, et al., "Loop-mediated isothethial amplification of DNA", NAR 28(12): e63 (2000))] wherein the at least one mesophilic enzyme for amplifying nucleic acids under isothemial conditions is selected from the group consisting of helicase, mesophilic polymerases, mesophilic polymerases having strand displacement activity, nicking enzymes, recombination proteins, ligases, glycosylases and nucleases.

"Helicases" are known by those skilled in the art. They are proteins that move directionally along a nucleic acid phosphodiester backbone, separating two annealed nucleic acid strands (e.g. DNA, RNA, or RNA-DNA hybrid) using energy derived from hydrolysis of NTPs or dNTPs, preferably ATP or dATP. Based on the presence of defined helicase motifs, it is possible to attribute a helicase activity to a given protein. The skilled artisan is able to select suited enzymes with helicase activity for the use in a method according to the present invention. In a preferred embodiment the helicase is selected from the group comprising helicases from different families (superfamily I helicases (e.g. dda, perA, F-plasmid tral protein helicase, uvrD, superfamily II helicases (e.g. recQ, NS3-helicase), superfamily III helicases (e.g. AAV rep Helicase), helicases from dnaB-like superfamily (e.g. T7 phage helicase) or helicases form rho-like superfamily In a preferred embodiment the mesophilic polymerase is selected from the group comprising phi29-polymerase, Bst-polymerase, Gst-polymerase, PyroPhage polymerase, Klenow polymerase, DisplaceAce Polymerase. All enzymes may be modified e.g. by eliminating nuclease activities or chemical modifications.

"Recombination proteins" in context of the present invention are proteins that are important for DNA recombination and repair processes and are known by those skilled in the art. They may e.g. be selected from the group comprising SSB, T4gp32, recA, single-stranded DNA translocases, double-stranded DNA translocases, nucleases, helicases, polymerases, ligases, and their homologues from different organisms.

"Glycosylases" in context of the present invention are enzymes that remove a base from a DNA strand. In a preferred embodiment the glycosylase is an uracil-N-glycosylase and removes uracil from a DNA strand.

"Nicking enzymes" in context of the present invention are enzymes that hydrolyse (cut), one strand of a double-stranded nucleic acid at a specific recognition nucleotide, sequences known as a restriction site. Nicking enzymes only cut one strand of the double stranded nucleic acid and do not cleave the double strand. Nicking enzymes are known by those skilled in the art and may e.g. be chosen from the group comprising Nb.BbvCI, Nb.BsmI, Nb.BsrDI, Nb.BtsI, Nt.AlwI, Nt.BbvCI, Nt.BsmAI, Nt.BspQI, Nt.BstNBI, Nt.CviPII.

By "strand displacement activity" it is meant that an enzyme is able to separate the strands of double stranded nucleic acids. In a preferred embodiment the mesophilic enzyme is a polymerase having strand displacement activity, i.e. the polymerase is able to displace the complementary strand from the template strand and thereby allows continuous polymerisation of a new strand. Several polymerases having strand displacement activity are known by the person skilled in the art. In a preferred embodiment of the present invention the polymerase having strand displacement activity is selected from the group of polymerases of phages selected from the group comprising phi29, Cp-1, PRD-1, Phi 15, Phi 21, PZE, PZA, Nf, M2Y, B103, SF5, GA-1, Cp-5, Cp-7, PR4, PR5, PR722 and L 17, or the polymerases Bst-polymerase, Gst-polymerase, PyroPhage polymerase, Vent-Polymerase, Deep-Vent Poylmerase, Klenow Polymerase, DisplaceAce Polymerase. The displacement activity of polymerases may be increased by modification (e.g. by elimination of the 5'-3'exonuclease activity).

"Ligases" in context of the present invention are enzymes that can covalently link two separate nucleic acid molecules at their sugar back bones, i.e. they link the 3' terminal OH of the first nucleic acid molecule covalently with the 5' terminal phosphate group of the second nucleic acid molecule to form a phosphodiester and thereby a continuous nucleic acid strand. Ligases can link single stranded nucleic acids as well as double stranded. Furthermore, ligases can close single strand breaks of double stranded nucleic acids, as for example generated by nicking enzymes. Ligases may be selected from the group comprising DNA-ligases and RNA-ligases. Suited ligases are known by those skilled in the art and can, e.g., be selected from the group comprising T4-Ligase, RNA ligase and thermostable polymerases.

It will be understood by those skilled in the art that in context of the present invention at least one of the above-mentioned enzymes used is mesophilic, i.e. other enzymes used in the method may be thermophilic as long as at least one enzyme involved in the amplification reaction is not. For example a thermophilic polymerase may be used together with a helicase. In this case the helicase is the at least one mesophilic enzyme.

The method according to the present invention is astonishingly well suited for different isothermal amplification methods. By embedding an essential component of the isothermal amplification reaction into the matrix the present invention provides an improved method for amplifying nucleic acid which overcomes the above-mentioned drawbacks of prior art methods. The method according to the present invention may be adapted for the desired isothermal amplification method. In a preferred embodiment of the present invention the method for isothermal amplification of nucleic acids is selected from the group comprising helicase-dependent amplification (HDA), thermostable HDA (tHDA), strand displacement amplification (SDA), multiple displacement amplification (MDA), rolling circle amplification, single primer isothermal amplification (SPIA), restriction aided RCA, transcription mediated amplification (TMA), and amplification reactions using nicking enzymes, nicking enzyme amplification reaction (NEAR), amplification reactions using recombination proteins, recombinase polymerase amplification (RPA), reverse transcription.

In the context of the present invention, a specific class of nucleic acid may be, inter alia, RNA, DNA, cDNA (complementary DNA), LNA (locked nucleic acid), mRNA (messenger RNA), mtRNA (mitochondrial RNA), rRNA (ribosomal RNA), tRNA (transfer RNA), nRNA (nuclear RNA), siRNA (short interfering RNA), snRNA (small nuclear RNA), snoRNA (small nucleolar RNA), scaRNA (Small Cajal Body specific RNA), microRNA, dsRNA (doubled-stranded RNA), ribozyme, riboswitch, viral RNA, dsDNA (double-stranded DNA), ssDNA (single-stranded DNA), plasmid DNA, cosmid DNA, chromosomal DNA, viral DNA, mtDNA (mitochondrial DNA), nDNA (nuclear DNA), snDNA (small nuclear DNA) or the like or any other class or sub-class of nucleic acid which is distinguishable from the bulk nucleic acid in a sample.

Oligonucleotide primers may be prepared using any suitable method, such as, for example, the phosphotriester and phosphodiester methods or automated embodiments thereof. In one such automated embodiment diethylophosphoramidites are used as starting materials and may be synthesized as described by Beaucage et al., Tetrahedron Letters, 22:1859-1862 (1981). One method for synthesizing oligonucleotides on a modified solid support is described in U.S. Pat. No. 4,458,006. It is also possible to use a primer which has been isolated from a biological source (such as a restriction endonuclease digest). Preferred primers have a length of from about 6 to 100, more preferably about 20 to 50, most preferably about 20 to 40 bases.

As used herein, the term "dNTP" refers to deoxyribonucleoside triphosphates. Non-limiting examples of such dNTPs are dATP, dGTP, dCTP, dTTP, dUTP, which may also be present in the form of labelled derivatives, for instance comprising a fluorescence label, a radioactive label, a biotin label. dNTPs with modified nucleotide bases are also encompassed, wherein the nucleotide bases are for example hypoxanthine, xanthine, 7-methylguanine, inosine, xanthinosine, 7-methylguanosine, 5,6-dihydrouracil, 5-methylcytosine, pseudouridine, dihydrouridine, 5-methylcytidine. Furthermore, ddNTPs of the above-described molecules are encompassed in the present invention.

As used herein, the term "NTP" refers to ribonucleoside triphosphates. Non-limiting examples of such NTPs are ATP, GTP, CTP, TTP, UTP, which may also be present in the form of labelled derivatives, for instance comprising a fluorescence label, a radioactive label, a biotin label.

Essential co-factors of isothermal amplification reactions are known by those skilled in the art and are dependent on the enzyme used. They may be organic or inorganic chemical compounds. Inorganic chemical compounds, for example, may be selected from the group comprising metal ions, Mg, Mn, Ca, Fe, Cu, Ni. Organic co-factors may be selected form the group of vitamins, proteins, biotin, nicotinamide adenine dinucleotide, and nucleotides, e.g. ATP.

The matrix comprising said at least one essential component may be provided in different forms within the kit according to the present invention. For example it may be provided as beads or the matrix may be comprised within a reaction vessel, e.g. at its bottom, in which the reaction shall take place. In one embodiment of the present invention the matrix comprising said at least one essential component for an isothermal amplification is lyophilised.

The matrix comprising the embedded mesophilic enzyme may be further modified, e.g. to regulate the release rate of the mesophilic enzyme. For example the matrix could be coated with one or more further matrixes, e.g. matrixes of a lower disintegrating temperature, giving a multi-layered matrix. Thus, in one embodiment the matrix comprising at least one essential component for the isothermal amplification reaction is coated with a second matrix. In a further embodiment further essential components of an isothermal amplification reaction are embedded in the second matrix. This allows multistep isothermal amplification reactions. For example the reaction mixture comprising the multi-layered matrix is first treated under conditions to disintegrate the second matrix resulting in the release of essential component(s) of the isothermal amplification reaction embedded therein, e.g. a first pair of primer. Thereafter, the reaction mixture is treated under conditions to allow amplification of the target nucleic acid by using the first pair of primer. After appropriate time, the mixture may be shifted to conditions under which the first matrix disintegrates and releases the therein embedded essential component(s), e.g. a second pair of primer (nested primer), followed by the incubation under conditions for the isothermal amplification reaction. Thereby, the present invention provides a method for sequential isothermal amplification without the need to reopen the reaction vessel to add components of the different amplification steps, e.g. nested primer.

However, the at least one component embedded in the matrix may be selected as desired. The skilled artisan is able adapt the present invention with respect to the embedded essential component of the isothermal amplification reaction. For example he may choose essential components which are not sensitive to room temperature to embed in the matrix. This would allow the storage of the matrix at room temperature. However, in a preferred embodiment the essential component in the matrix is selected from the group comprising said mesophilic enzyme for amplifying nucleic acids under isothermal conditions, dNTP and/or NTPs, essential co-factors, and at least one primer for amplification of the target nucleic acid.

In a preferred embodiment of the method for embedding mesophilic enzymes the matrix is solubilised by incubation at temperatures of at least 40° C., preferably at least 50° C., more preferably at least 65° C. It will be acknowledged by those skilled in the art that the matrix can be solubilised at a relative high temperature, e.g. 65° C., but the mixing with said solution comprising at least one mesophilic enzyme may be performed at a lower temperature, provided that the matrix material does not solidify. In a preferred embodiment the mixing is performed at a temperature between 40° C. to 70° C.

After appropriate mixing the matrix and the solution comprising at least one mesophilic enzyme will form a homogeneous mixture. Thereafter, the matrix within said mixture shall solidify. Thus, the matrix-enzyme mixture is incubated under conditions that allow the solidification of the matrix to obtain the embedded mesophilic enzyme. In a preferred embodiment the matrix-enzyme mixture is incubated at a temperature of 50° C. or less, preferably 40° C. or less, more preferably 30° C. or less, even more preferably 20° C. or less.

The matrix may be further processed after the embedding of the mesophilic enzyme(s). In one embodiment of the present invention the method for embedding further comprises the step of lyophilization of the embedded mesophilic enzyme.

The present invention also relates to the use of a composition and/or a kit according to the present invention in a method selected from the group comprising isothermal nucleic acid amplification, helicase-dependent amplification (HDA), thermostable HDA (tHDA), strand displacement amplification (SDA), multiple displacement amplification (MDA), rolling circle amplification, single primer isothermal amplification (SPIA), restriction aided RCA, transcription mediated amplification (TMA), and nicking enzyme amplification reaction (NEAR), and a method according to the present invention.

EXAMPLES

Example 1

Reduction of Unspecific Products by Embedding Primers in the Matrix

A solution comprising 2.0% low melting agarose (Sigma Aldrich GmbH, Germany) was mixed with primers and probes specific for *Clamydia trachomatis* and *Neisseria gonorrhoea* (*N. gonorrhoea* specific primer: NG opaDv F1, NG opaDv R; *C. trachomatis* specific primer: CT-p1 F9, CT-p1 R17; FAM-labelled *C. trachomatis* specific probe: CT-p1 p6 FAM; TEX-labelled *N. gonorrhoea* specific probe: NG opaD b1 TEX). The mixture is subsequently heated to 65° C. to obtain melted agarose/primer/probe mixture. 15 µl of the melted agarose/primer/probe mixture was applied to a reaction vessel and cooled. Thereby a hydrogel comprising primer and probes formed on the bottom of the vessel. The final agarose concentration of the matrix was 1.0%). Reaction vessels containing the above mentioned primer and probes without agarose served as reference.

TABLE 1

Primer and probe sequences

| Name | Sequence | SEQ ID NO. |
| --- | --- | --- |
| NG opaDv F1 | ACCCGATATAATCCGTCCT TCA | 1 |
| NG opaDv R | CGGCTCCTTATTCGGTTTA ACC | 2 |
| NG opaD b1 TEX | CGTCCTTCAACATCAGTGA AAATCG | 3 |
| CT-p1 F9 | AGGCGATTTAAAAACCAAG GTCGATGT | 4 |

TABLE 1-continued

Primer and probe sequences

| Name | Sequence | SEQ ID NO. |
|---|---|---|
| CT-pl R17 | GAAGAAATTGATCCAACAC CCTTATCG | 5 |
| CT-pl p6 FAM | CCGTATGTGGAATGTCGAA CTCATCGG | 6 | tHDA reaction mixture was added to the reaction vessel to obtain a final concentration of 6 mM MgSO$_4$, 40 mM NaCl, 0.6 mM dNTP, 6 mM dATP, 140 mM DMSO, 150 mM Sorbitol, 1× annealing buffer (BioHelix), primer and probes (concentration see below), 1.75 µl enzyme mix (enzyme mix comprised helicase and polymerase, provided with tHDA Kit from BioHelix). Target DNA (1000 copies) from *C. trachomatis* and *N. gonorrhoea* was added to the reaction tubes. Reaction mixtures without target DNA served as no template control (NTC).

The reaction mixtures were heated to 65° C. and incubated for 90 min at this temperature resulting in the disintegration of the agarose and isothermal amplification of the target DNA. The amount of amplified target DNA was determined using the fluorescent probes (FIG. 1).

TABLE 2

Primer and probe concentrations

|  | Final concentration (µM) in tHDA reaction |
|---|---|
| NG opaDv F1 TIB | 0.04 |
| NG opaDv R TIB | 0.12 |
| NG opaD b1 TIB TEX | 0.06 |
| CT-pl F9 TIB | 0.04 |
| CT-pl R17 TIB | 0.12 |
| CT-pl p6 FAM TIB | 0.06 |

The background signal of the negative controls was tremendously decreased by applying primer and probes embedded in an agarose matrix. Furthermore, the fluorescence signals of the reactions containing target DNA and embedded primer and probes were significantly higher than the signals of the references. This clearly shows that specificity as well as sensitivity of isothermal amplification reactions are increased when essential components are embedded in a matrix disintegrating a predetermined condition, i.e. temperatures of 65° C. or higher.

Example 2

Reduction of Unspecific Products by Embedding Mesophilic Enzymes in the Matrix

A solution comprising 2.0% low melting agarose (Sigma Aldrich GmbH, Germany) was melted and subsequently mixed with 0.5 µl Helicase (500 ng/µl) and 1 µl Gst Polymerase (200 U/µl). 9.5 µl of the received mixture was applied to a reaction vessel and cooled. A hydrogel comprising primer and probes formed on the bottom of the vessel. The final agarose concentration of the matrix was 1.7%. Reaction vessels containing the matrix without helicase and polymerase served as reference. After solidification of the matrix tHDA reaction mixture was applied to the vessel. The final concentration of the reaction mixture within the vessel was 3.5 mM MgSO4, 40 mM NaCl, 0.4 mM dNTP, 3 mM dATP, 97 mM betaine, 1× annealing buffer (BioHelix) and EvaGreen (0.2×). Helicase and polymerase were additionally applied to the reference. For detection of p53 from human DNA primer "TP53 for" (att tga tgc tgt ccc cgg acg ata tt; SEQ ID NO. 7) and "TP53 rev" (cat tct ggg agc ttc atc tgg acc tg; SEQ ID NO. 8) were used in a final concentration of 0.1 µM each. 100 ng of human DNA was applied to the reaction vessels except for no-template controls (NTC). The reaction vessels were incubated at 65° C. for 90 minutes in a Real-time Cycler (BioRad CFX). The CT-values indicate the time point (min) at which the fluorescence signal was detectable over the threshold value. A high CT-value indicates low abundance of the amplification product while a low CT-value is indicative for high abundance of the amplification product. The difference between the CT-values of the reactions with template and the NTC reactions were used to determine the signal/noise ratio. Desirable is a high difference between the CT-values (Delta-CT).

Figure 2:
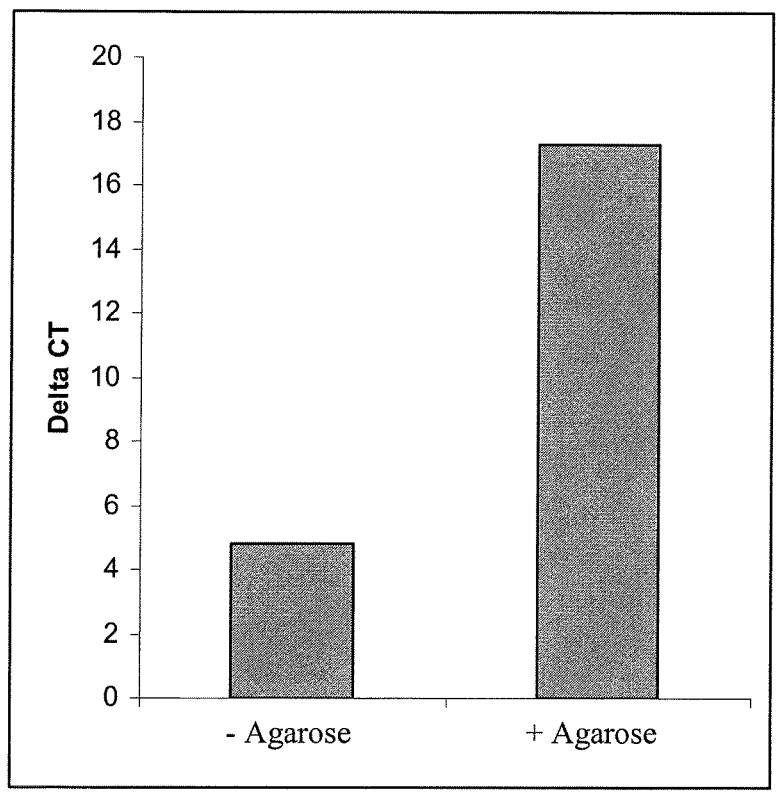

Results:

Higher Delta-CT values are observed in reaction where essential components (helicase and polymerase) were separated from the other reaction components by embedding in agarose (FIG. 2). This clearly shows that the signal/noise ratio, i.e. the sensitivity, of isothermal amplification reactions can be drastically enhanced by the method according to the present invention.

FIGURE LEGENDS

FIG. 1: FIG. 1 shows the results of example 1. If the reaction is started with primers and probes embedded in agarose, the fluorescence is higher in those reactions comprising 1000 k of target DNA. The fluorescence is lower in the no-template-controls (NTC). This indicated that the signal-to-noise ration was increased if primers and probes were embedded in agarose.

FIG. 2: FIG. 2 shows the result of example 2. The CT-values indicate the time point (min) at which the fluorescence signal was detectable over the threshold value. A high CT-value indicates low abundance of the amplification product while a low CT-value is indicative for high abundance of the amplification product. The difference between the CT-values of the reactions with template and the NTC reactions were used to determine the signal/noise ratio. Desirable is a high difference between the CT-values (Delta-CT).

The invention claimed is:

1. A method for isothermal amplification of nucleic acids comprising the steps of:
   i) providing at least the following reaction components:
      a) a mesophilic enzyme for amplifying nucleic acids under isothermal conditions;
      b) one or more primer for amplifying a target nucleic acid;
      c) dNTPs or NTPs;
      d) essential co-factors or reagents of the enzyme for amplifying nucleic acids under isothermal conditions;
      e) at least one target nucleic acid; wherein at least one of the reaction components a) to e) is embedded in a matrix, wherein said matrix disintegrates at temperatures of 60° C. or more;
   ii) incubating the reaction components under conditions which result in the disintegration of said matrix in order to obtain the reaction mixture;
   iii) incubating the reaction mixture under conditions suited for the isothermal amplification reaction; wherein the incubation temperature under step ii) is 1° C. to 50° C. higher than the incubation temperature of step iii.

2. The method according to claim 1, wherein the mesophilic enzyme for amplifying nucleic acids has an optimum temperature of 20° C. to 70° C.

3. The method according to claim 1, wherein the matrix forms a hydrogel.

4. The method according to claim 1, wherein the matrix is selected from the group comprising polysaccharides, proteins, wax and synthetic polymers.

5. The method according to claim 1, wherein the at least one mesophilic enzyme for amplifying nucleic acids under isothermal conditions is selected from the group comprising helicase, mesophilic polymerases, mesophilic polymerases having strand displacement activity, nicking enzymes, recombination proteins, ligases, glycosylases and nucleases.

6. The method according to claim 1, wherein the method for isothermal amplification of nucleic acids is selected from the group comprising helicase-dependent amplification (HDA), thermostable HDA (tHDA), strand displacement amplification (SDA), multiple displacement amplification (MDA), rolling circle amplification, single primer isothermal amplification (SPIA), restriction aided RCA, transcription mediated amplification (TMA), and amplification reactions using nicking enzymes, nicking enzyme amplification reaction (NEAR), amplification reactions using recombination proteins, recombinase polymerase amplification (RPA).

7. The method of claim 1, wherein the incubation temperature under step ii) is 5° C. to 25° C. higher.

8. The method of claim 1, wherein the incubation temperature under step ii) is 10° C. to 20° C. higher.

9. The method of claim 2, wherein the optimum temperature is 30° C. to 65° C.

10. The method of claim 2, wherein the optimum temperature is 37° C. to 60° C.

11. The method of claim 4, wherein the polysaccharides is agarose, low-melting agarose, pectin, amylose, agar-agar, xanthan, carrageen, carboxymethylcellulose, guar, carubin, inulin, or dextran, wherein the proteins are gelatin or fibrillar proteins, and wherein the wax and synthetic polymers are polyvinylalcohol or derivates of cellulose.

* * * * *